United States Patent [19]

Ashton et al.

[11] Patent Number: 4,507,315
[45] Date of Patent: Mar. 26, 1985

[54] HYPOGLYCAEMIC AND HYPOLIPIDAEMIC BENZAMIDE SUBSTITUTED (1H-) IMIDAZOLE DERIVATIVES AND COMPOSITIONS

[75] Inventors: Michael J. Ashton, Chelmsford; David C. Cook, London; Colin J. Daniels, Romford; Anthony H. Loveless, Hornchurch; Jeremy D. Pratt, Romford; Bernard T. Bull, Launceston, all of England

[73] Assignee: May & Baker Limited, Essex, England

[21] Appl. No.: 525,503

[22] Filed: Aug. 22, 1983

[30] Foreign Application Priority Data

Aug. 24, 1982 [GB] United Kingdom ............... 8224296

[51] Int. Cl.$^3$ .................... A61J 31/415; C07D 233/54
[52] U.S. Cl. ...................................... 514/396; 548/341
[58] Field of Search .............................. 548/341, 337; 424/273 R

[56] References Cited

U.S. PATENT DOCUMENTS

| | | | |
|---|---|---|---|
| 3,349,124 | 10/1967 | McLamore | 260/553 |
| 4,113,871 | 9/1978 | Stach et al. | 424/272 |
| 4,221,815 | 9/1980 | Weyer et al. | 424/219 |
| 4,238,506 | 12/1980 | Stach et al. | 424/319 |
| 4,245,120 | 1/1981 | Shepherd | 424/263 |
| 4,317,915 | 3/1982 | Confalone et al. | 424/275 |
| 4,322,439 | 3/1982 | Klemm et al. | 424/319 |
| 4,328,155 | 5/1982 | Masaru et al. | 424/274 |
| 4,328,344 | 5/1982 | Masaru et al. | 424/274 |
| 4,330,472 | 5/1982 | Ogata et al. | 424/274 |
| 4,350,635 | 9/1982 | Ogata et al. | 424/274 |
| 4,351,770 | 9/1982 | Ogata et al. | 424/274 |

OTHER PUBLICATIONS

D. Steinberg, J. Pathology, vol. 133, (1981), pp. 75–87.

Day et al., Advances in Experimental Medicine and Biology, vol. 109, (1981), pp. 277–283.

Primary Examiner—Henry R. Jiles
Assistant Examiner—J. G. Mullins
Attorney, Agent, or Firm—Stevens, Davis, Miller & Mosher

[57] ABSTRACT

Benzamide derivatives of the general formula:

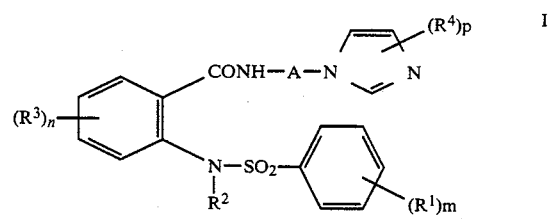

wherein A represents a divalent straight- or branched-chain alkylene group containing from 1 to 6 carbon atoms and $R^1$ represents a halogen atom or a hydroxy, mercapto, amino, nitro, cyano, carboxy or carbamoyl group or an alkyl, fluorine-substituted alkyl, alkoxy, alkylthio, alkylsulphinyl, alkylsulphonyl, alkoxycarbonyl, alkylamino, dialkylamino, alkylcarbamoyl, dialkylcarbamoyl, alkanoyl, alkanoyloxy or alkanoylamino group and m represents zero or the integer 1, 2 or 3, $R^2$ represents a hydrogen atom or an alkyl group, $R^3$ represents a halogen atom or a hydroxy, amino, nitro, cyano, carboxy or carbamoyl group or an alkyl, fluorine-substituted alkyl, alkoxy, alkoxycarbonyl, dialkylamino, alkylcarbamoyl or alkanoylamino group and n represents zero or the integer 1 or 2, $R^4$ represents and alkyl radical and p represents zero or the integer 1 or 2, or a pharmaceutically acceptable salt thereof, possess useful pharmacological properties.

14 Claims, No Drawings

HYPOGLYCAEMIC AND HYPOLIPIDAEMIC BENZAMIDE SUBSTITUTED (1H-) IMIDAZOLE DERIVATIVES AND COMPOSITIONS

DESCRIPTION

This invention relates to new therapeutically useful benzamide derivatives, to processes for preparing them, and to pharmaceutical compositions containing them.

The benzamide derivatives of the present invention are those compounds of the general formula:

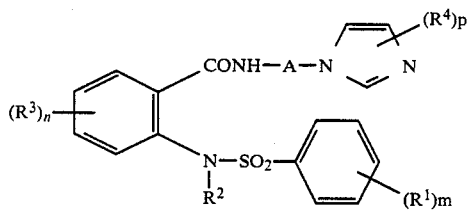

wherein A represents a divalent straight- or branched-chain alkylene group containing from 1 to 6, preferably 2, 3, or 4, carbon atoms and $R^1$ represents a halogen, i.e. fluorine, chlorine, bromine or iodine, atom or a hydroxy, mercapto, amino, nitro, cyano, carboxy or carbamoyl group or an alkyl, fluorine-substituted alkyl (e.g. trifluoromethyl), alkoxy, alkylthio, alkylsulphinyl, alkylsulphonyl, alkoxycarbonyl, alkylamino, dialkylamino, alkylcarbamoyl, dialkylcarbamoyl, alkanoyl, alkanoyloxy or alkanoylamino group and m represents zero or the integer 1, 2 or 3, $R^2$ represents a hydrogen atom or an alkyl group, $R^3$ represents a halogen atom or a hydroxy, amino, nitro, cyano, carboxy or carbamoyl group or an alkyl, Fluorine-substituted alkyl, e.g. trifluoromethyl, alkoxy, alkoxycarbonyl, dialkylamino, alkylcarbamoyl or alkanoylamino group and n represents zero or the integer 1 or 2, $R^4$ represents an alkyl radical and p represents zero or the integer 1 or 2, and pharmaceutically acceptable salts thereof.

Fluorine-substituted alkyl groups within the definitions of the substituents $R^1$ and $R^3$ may be substituted by one or more fluorine atoms. Alkyl groups or moieties, alkoxy groups or moieties and alkanoyl groups or moieties above may be straight- or branched-chain and contain from 1 to 10 (preferably 1 to 4) carbon atoms. The alkyl moieties in the dialkylamino and dialkylcarbamoyl groups above may be the same or different.

When any of the symbols m, n and p represent the integer 2 or 3, the groups represented by the corresponding symbol $R^1$, $R^3$ or $R^4$ may be the same or different.

In certain cases the substituents $R^1$, $R^2$, $R^3$, $R^4$ and alkylene group A contribute to optical isomerism. All such forms are embraced by the present invention.

By the term "pharmaceutically acceptable salt" in relation to compounds of general formula I is meant a salt formed by reaction with an acid or, when $R^1$ or $R^3$ represents a carboxy group, by reaction with a base, so that the anion (in the case of an acid addition salt) or the cation (in the case of a salt formed by a compound of general formula I wherein $R^1$ or $R^3$ represents a carboxy group) is relatively innocuous to the animal organism when used in therapeutic doses so that the beneficial pharmacological properties of the parent compound of general formula I are not vitiated by side-effects ascribable to the said anion or cation.

Suitable acid addition salts include salts derived from inorganic acids, for example hydrochlorides, hydrobromides, phosphates, sulphates and nitrates, and organic salts, for example methanesulphonates, 2-hydroxyethanesulphonates, oxalates, lactates, tartrates, acetates, salicylates, citrates, propionates, succinates, fumarates, maleates, methylene-bis-β-hydroxynaphthoates, gentisates and di-p-toluoyltartrates.

Suitable salts formed by compounds of general formula I wherein $R^1$ or $R^3$ represents a carboxy group include the alkali metal (e.g. sodium and potassium), alkaline earth metal (e.g. calcium and magnesium), and ammonium salts, and salts of amines known in the art to be pharmaceutically acceptable, e.g. ethylene diamine, choline, diethanolamine, triethanolamine, octadecylamine, diethylamine, triethylamine, 2-amino-2-(hydroxymethyl)propane-1,3-diol and 1-(3,4-dihydroxyphenyl)-2-isopropylaminoethanol.

It is to be understood that, where in this specification reference is made to compounds of general formula I, it is intended to refer also to their pharmaceutically acceptable salts as indicated above, where the context so permits.

Preferred compounds of general formula I are those wherein A represents an ethylene, trimethylene, 3-methyltrimethylene or tetramethylene group and $R^1$ represents a halogen atom or an amino, nitro, trifluoromethyl or acetamido group or an alkyl, e.g. methyl, alkoxycarbonyl or $C_{1-4}$ alkoxy group and m represents zero or the integer 1, 2 or 3, $R^2$ represents a hydrogen atom, $R^3$ represents a halogen, preferably chlorine, atom and n represents zero or the integer 1, and $R^4$ represents an alkyl, e.g. methyl, group in the 2- or 4-position and p represents zero or the integer 1.

Especially preferred compounds of general formula I are those wherein A represents an ethylene, trimethylene or 3-methyltrimethylene group and $R^1$ represents a halogen atom, trifluoromethyl group, or an alkyl, e.g. methyl, group and m represents the integer 1 or 2, $R^2$ represents a hydrogen atom, $R^3$ represents a halogen, preferably chlorine atom and n represents zero or the integer 1, and $R^4$ represents an alkyl, e.g. methyl, group in the 4-position and p represents zero or the integer 1. When m is the integer 1, the group $R^1$ is in preferably the 2, 3 or 4-position, or 3-position when $R^1$ represents a trifluoromethyl group. When m is the integer 2, the groups $R^1$ are preferably the same and in positions 2,4; 3,4 or 2,5 when halogen atoms and in positions 3,4 when methyl groups. The symbol A preferably represents trimethylene.

The compounds of general formula I possess useful pharmacological properties, in particular hypoglycaemic activity, and some are intermediates for the preparation of the other therapeutically useful derivatives. The compounds of general formula I lower blood glucose levels in mice suffering from diabetes mellitus. They lower the concentrations of cholesterol and of triglycerides in the blood. Thus, they are of utility in the prevention or treatment of diabetes mellitus, hyperlipoproteinaemic states and of atherosclerosis.

Compounds of general formula I which are of particular interest include the following compounds, and their salts:

| Compound | |
|---|---|
| A | 2-(4-chlorobenzenesulphonamido)-N—(3-imidazol- |

| Compound | |
|---|---|
| B | 2-(3-chlorobenzenesulphonamido)-N—(3-imidazol-1-ylpropyl)benzamide |
| C | 2-(2-chlorobenzenesulphonamido)-N—(3-imidazol-1-ylpropyl)benzamide |
| D | 2-(4-bromobenzenesulphonamido)-N—(3-imidazol-1-ylpropyl)benzamide |
| E | 2-(benzenesulphonamido)-N—(3-imidazol-1-ylpropyl)-benzamide |
| F | 2-(4-methylbenzenesulphonamido)-N—(3-imidazol-1-ylpropyl)benzamide |
| G | 2-(3,4-dimethylbenzenesulphonamido)-N—(3-imidazol-1-ylpropyl)benzamide |
| H | 2-(4-nitrobenzenesulphonamido)-N—(3-imidazol-1-ylpropyl)benzamide |
| I | 5-chloro-2-(4-chlorobenzenesulphonamido)-N—(3-imidazol-1-ylpropyl)benzamide |
| J | 2-(2,5-dichlorobenzenesulphonamido)-N—(3-imidazol-1-ylpropyl)benzamide |
| K | 2-(2-nitrobenzenesulphonamido)-N—(3-imidazol-1-ylpropyl)benzamide |
| L | 2-(4-fluorobenzenesulphonamido)-N—(3-imidazol-1-ylpropyl)benzamide |
| M | 2-(4-chlorobenzenesulphamido)-N—[3-(2-methyl-imidazol-1-yl)-propyl]benzamide |
| N | 2-(4-chlorobenzenesulphonamido)-N—[3-(4-methyl-imidazol-1-yl)-propyl]benzamide |
| O | 2-(4-nitrobenzenesulphonamido)-N—[3-(4-methyl-imidazol-1-yl)propyl]-benzamide |
| P | 2-(4-aminobenzenesulphonamido)-N—(3-imidazol-1-ylpropyl)benzamide |
| Q | 2-(4-methoxybenzenesulphonamido)-N—(3-imidazol-1-ylpropyl)benzamide |
| R | 2-(4-acetamidobenzenesulphonamido)-N—(3-imidazol-1-ylpropyl)benzamide |
| S | 2-(4-isopropylbenzenesulphonamido)-N—(3-imidazol-1-ylpropyl)benzamide |
| T | 2-(4-t-butylbenzenesulphonamido)-N—(3-imidazol-1-ylpropyl)benzamide |
| U | 2-(4-octylbenzenesulphonamido)-N—(3-imidazol-1-ylpropyl)benzamide |
| V | 2-(4-ethoxycarbonylbenzenesulphonamido)-N—(3-imidazol-1-ylpropyl)benzamide |
| W | 2-(-3-trifluoromethylbenzenesulphonamido)-N—(3-imidazol-1-ylpropyl)-benzamide |
| X | 2-(3,4-dichlorobenzenesulphonomido)-N— (3-imidazol-1-ylpropyl)benzamide |
| Y | 2-(2,4-dichlorobenzenesulphonamido)-N—(3-imidazol-1-ylpropyl)benzamide |
| Z | 2-(2,6-dichlorobenzenesulphonamido)N—(3-imidazol-1-ylpropyl)benzamide |
| AA | 2-(2,3-dichlorobenzenesulphonamido)-N—(3-imidazol-1-ylpropyl)benzamide |
| BB | 2-(2-trifluoromethylbenzenesulphonamido)-N—(3-imidazol-1-ylpropyl)benzamide |
| CC | 2-(4-chloro-2-trifluoromethylbenzenesulphonamido)-N—(3-imidazol-1-ylpropyl)benzamide |
| DD | 2-(3,5-bistrifluoromethylbenzenesulphonamido)-N—(3-imidazol-1-ylpropyl)benzamide |
| EE | 2-(2,4,5-trichlorobenzenesulphonamido)-N—(3-imidazol-1-ylpropyl)benzamide |
| FF | 2-(2,3,4-trichlorobenzenesulphonamido)-N—(3-imidazol-1-ylpropyl)benzamide |
| GG | 2-(4-chloro-3-trifluoromethylbenzenesulphonamido)-N—(3-imidazol-1-ylpropyl)benzamide |
| HH | 5-chloro-2-(3-trifluoromethylbenzenesulphonamido)-N—(3-imidazol-1-ylpropyl)benzamide |
| II | 5-chloro-2-(3,5-bistrifluoromethylbenzenesulphonamido)-N—(3-imidazol-1-ylpropyl)benzamide |
| JJ | 5-chloro-2-(3-chlorobenzenesulphonamido)-N—(3-imidazol-1-ylpropyl)benzamide |
| KK | 2-(3-fluorobenzenesulphonamido)-N—(3-imidazol-1-ylpropyl)benzamide |
| LL | 2-(3-fluoro-4-methylbenzenesulphonamido)-N—(3-imidazol-1-ylpropyl)benzamide |
| MM | 2-(3-bromobenzenesulphonamido)-N—(3-imidazol-1-ylpropyl)benzamide |
| NN | 2-(3-nitrobenzenesulphonamido)-N—(3-imidazol-1-ylpropyl)benzamide |
| OO | 2-(2,4-difluorobenzenesulphonamido)-N—(3-imidazol-1-ylpropyl)benzamide |
| PP | 2-(3-methylbenzenesulphonamido)-N—methylbenzenesulphonamido)-N—(3-imidazol-1-ylpropyl)benzamide |
| QQ | 2-(2-methylbenzenesulphonamido)-N—(3-imidazol-1-ylpropyl)benzamide |
| RR | 2-(2-fluorobenzenesulphonamido)-N—(3-imidazol-1-ylpropyl)benzamide |
| SS | 2-(2-chloro-5-irifluoromethylbenzenesulphonamido)-N—(3-imidazol-1-ylpropyl)benzamide |
| TT | 2-(4-iodobenzenesulphonamido)-N—(3-imidazol-1-ylpropyl)benzamide |
| UU | 2-(4-chlorobenzenesulphonamide)N— (4-imidazol-1-ylbutyl)benzamide |
| VV | 2-(4-chlorobenzenesulphonamido)-N—(2-imidazol-1-ylethyl)benzamide |
| WW | 2-(4-chlorobenzenesulphonamido)-N—(3-imidazol-1-ylbutyl)benzamide |

The letters A to WW are assigned to the compounds for easy reference later in the specification, for example in the following Tables.

Compounds A, W and W hydrochloride are preferred compounds of the invention.

The pharmacological properties of the compounds of general formula I or salts thereof are demonstrated in the following tests:

Hypoglycaemic Activity in Diabetic Mice

Diabetic mice (strain C 57, black, MRI derived Obese/Obese) of either sex each weighing between 45 and 70 g were given the test compound orally in tragacanth mucilage at a dose of 5,10,30,100,200 or 500 mg/kg body weight per day for 3 days. Three hours after the last dose the animals were killed with carbon dioxide and bled by cardiac puncture.

The blood glucose levels were assessed by the glucose-oxidase method of GOD-Perid.

Control groups (given doses of unmedicated tragacanth mucilage) were included with each test.

The percentage reduction in the concentration of blood glucose was calculated by comparison with the simultaneous controls, for each of the test compounds used.

The results obtained are shown in the following Table I.

TABLE 1

| Compound mg/kg body weight per day | change in blood glucose compared with control |
|---|---|
| A  200; 100; 30 | −67  −61;  −49;  −13 |
| F  200 | −32 |
| B  200 | −60 |
| G  200 | −25 |
| I  200 | −57 |
| J  200 | −42 |
| N  200 | −48 |
| VV  200 | −53 |
| WW  200 | −24 |
| W  200 | −68 |
| W  500; 200; 100; 30; 10; 5 hydrochloride | −46;  −62;  −50;  −58;  −29;  −25 |
| X  200 | −58 |
| Y  200 | −51 |
| OO  200 | −35 |
| QQ  200 | −43 |

Hypoglycaemic Activity in Diabetic Mice

Groups of diabetic mice (strain C 57, black, MRI derived Obese/Obese) of male sex of mean weight between 43 and 46 g were given the test compound W hydrochloride orally in tragacanth mucilage at a dose of 2, 5 or 100 mg/kg body weight per day for 8 days. Three hours after the last dose the animals were bled from the tail vein.

The blood glucose levels were assessed by the glucose-oxidase method of GOD-Perid.

Control groups (given doses of unmedicated tragacanth mucilage) were included with each test.

The percentage reduction in the concentration of blood glucose was calculated by comparison with the simultaneous controls.

The results obtained are shown in the following Table IA.

TABLE IA

| Dose mg/kg body weight per day | % change in blood glucose compared with control |
| --- | --- |
| 2 | −25 |
| 5 | −28 |
| 100 | −50 |

Hypoglycaemic Activity in Fasted Rats

Rats (Sprague-Dawley) of male sex each weighing between 171 and 174 g were given the test compound W hydrochloride orally in tragacanth mucilage at a dose of 100 mg/kg body weight per day for 4 days. Four hours after the third dose the animals were kept without food up to and beyond the fourth dose. Three hours after the last dose the animals were bled from the tail vein.

The blood glucose levels were assessed by the glucose-oxidase method of GOD-Perid.

Control groups (given doses of unmedicated tragacanth mucilage) were included with each test.

The percentage reduction in the concentration of blood glucose was calculated by comparison with the simultaneous controls.

The results obtained are shown in the following Table IB.

TABLE 1B

| Dose mg/kg body weight per day | % change in blood glucose compared with control |
| --- | --- |
| 100 | −26 |

Hypolipidaemic Activity in Rats

Male Wistar rats each weighing between 120 and 150 g were caged in groups of eight and fed a pelleted diet incorporating 0.5% w/w cholesterol and 0.25% w/w cholic acid for 10 days. For the last 3 days of that period the test compound was administered orally at a dose of 30, 100 or 200 mg/kg body weight per day in tragacanth mucilage.

At noon on day 10 the animals were killed by inhalation of carbon dioxide from solid carbon dioxide. A sample of blood was removed by cardiac puncture and the serum cholesterol and serum triglycerides were analysed by means of an auto-analyser.

Control group (receiving only doses of unmedicated tragacanth mucilage) were included with each test.

The percentage reductions in the concentrations of serum cholesterol and serum triglycerides were calculated by comparison with the simultaneous controls, for each concentration of the test compound used.

The results obtained are shown in Table II hereafter.

TABLE II

| Compound mg/kg body weight per day | % change in serum compared with control | |
| --- | --- | --- |
| | cholesterol | triglycerides |
| A 200 | −82, −82, −83 | −85, −89, −75 |
| 100 | −35 | +36 |
| 30 | −13 | +67 |
| D 200 | −63 | −59 |
| E 200 | −31 | +55 |
| F 200 | −72 | −60 |

The utility of the compounds is enhanced by the fact that they are of only very low toxicity, as demonstrated in the following test:

Oral Toxicity in Mice

Groups of mice were dosed orally with graded doses of the test compound (in a 0.5% w/v aqueous suspension of tragacanth mucilage) and observed for 3 days thereafter. The percentage of animals which died during that period at each dose level were used to construct a graph, from which the LD 50, that is to say the dose in mg/kg animal body weight necessary to kill 50% of the mice, was calculated.

Compounds of the present invention were tested and the LD 50 of each compound was greater than 1000 mg/kg body weight.

The compounds of general formula I can be prepared by the application or adaptation of known methods (i.e. methods heretofore used or described in the chemical literature), for example as hereinafter identified.

(A) According to a feature of the present invention, the compounds of general formula I are prepared by the reaction of a compound of the general formula:

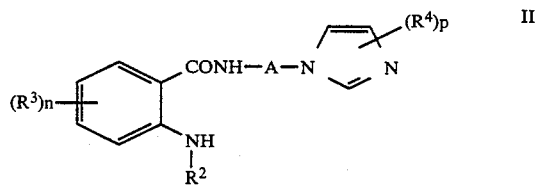

II (wherein A, $R^2$, $R^3$, $R^4$, n and p are as hereinbefore defined) with a sulphonating agent of the general formula:

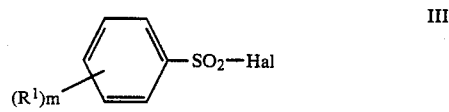

III wherein $R^1$ and m are as hereinbefore defined and Hal represents a halogen, preferably chlorine, atom.

The reaction above is generally carried out in water or an organic solvent optionally in the presence of a base for example a trialkylamine, e.g. triethylamine, or pyridine, at a temperature between 0° C. and the reflux temperature of the reaction mixture. An excess of the base may serve as solvent for the reaction.

(B) According to another feature of the present invention, the compounds of general formula I are prepared by the reaction of a compound of the general formula:

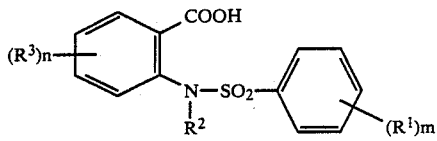

(wherein $R^1$, $R^2$, $R^3$, m and n are as hereinbefore defined) or a reactive derivative, e.g. acid chloride or acid ester, thereof (optionally prepared in situ) with a compound of the general formula:

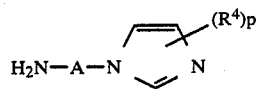

(wherein A, $R^4$ and p are as hereinbefore defined).

The reaction above is generally carried out in an inert organic solvent e.g. dimethylformamide or dioxan, and preferably in the presence of an acid binding agent, for example a trialkylamine, e.g. triethylamine, at a temperature which may be greater than ambient temperature, for example at between 10° C. and 50° C.

The acid chloride may be prepared by the reaction of a compound of general formula IV with thionyl chloride by the application or adaption of known methods.

The compounds of general formula II may be prepared by reacting a compound of general formula V with a compound of the general formula:

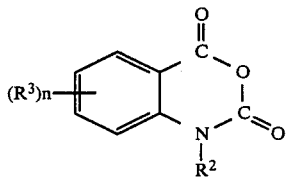

(wherein $R^2$, $R^3$ and n are as hereinbefore defined) or a compound of the general formula:

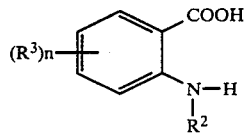

(wherein $R^2$, $R^3$ and n are as hereinbefore defined) or a reactive derivative, e.g. acid chloride, thereof in a similar manner to that hereinbefore described in (B).

The compounds of general formula IV may be prepared by reacting a compound of general formula III with a compound of general formula VII in a similar manner to that hereinbefore described in (A).

The compounds of general formulae III, V, VI and VII are known compounds or may be prepared by the application or adaptation of known methods.

According to a feature of the present invention the compounds of general formula I are converted to their pharmaceutically acceptable salts, and vice versa, by the application or adaptation of known methods.

As well as being useful in itself, this procedure is useful for the purification of compounds of general formula I and their salts by taking advantage of differences in solubility in water and various organic solvents of the compounds and their salts and of any impurities present, by means of known methods such as crystallisation.

(i) Compounds of general formula I wherein $R^1$ or $R^3$ represents a carboxy group may be converted to their salts of pharmaceutically acceptable bases, for example, by reaction with the appropriate base, for example the appropriate amine or a compound of the general formula:

$$M^1OR \qquad VIII$$

(wherein $M^1$ represents an alkali metal, e.g. sodium or potassium, atom and R represents an alkyl group containing up to 4 carbon atoms, e.g. methyl or ethyl, or a hydrogen atom) in a suitable solvent, e.g. methanol or ethanol, or a mixture of water and acetone; followed if necessary by evaporation of part or all of the solvent, and collection of the solid salt.

These salts may be converted to the parent compounds of general formula I, for example by reaction with a suitable acid, e.g. glacial acetic acid, in solution in a suitable solvent, e.g. water or ethanol, followed if necessary by evaporation of part or all of the solvent, and collection of the solid compound of general formula I.

(ii) Compounds of general formula I may be converted to their pharmaceutically acceptable acid addition salts, for example, by reaction with the appropriate acid in solution or suspension in a suitable solvent, e.g. acetone, methanol or ethanol, followed if necessary by evaporation of part or all of the solvent, and collection of the solid salt.

The acid addition salts may be converted to the parent compounds of general formula I, for example by reaction with aqueous ammonia in the presence of a suitable solvent, e.g. ethanol, followed by treatment with a weak acid, for example glacial acetic acid.

It will be understood by those skilled in the art that in the performance of the processes described above of the present invention it may be desirable to introduce chemical protecting groups into the reactants in order to avoid secondary reactions taking place, for example, in the methods of preparation of derivatives hereinbefore described hydroxy substituent(s) within the definition of the groups $R^1$ and $R^3$ as defined in relation to general formula I may have been converted into benzyloxy groups before reaction as described with subsequent removal of the protecting benzyl groups.

It is to be understood that the amino, alkylamino, carboxy and hydroxy groups which are present in certain reactants may be protected by any protective groups which are usually employed for protecting amines, carboxylic acids or alcohols, and whose use does not adversely affect the remainder of the molecule.

By way of examples, the amino and alkylamino groups can be protected by radicals such as tert-butoxycarbonyl; 2,2,2-trichloroethoxycarbonyl, trichloroacetyl, trityl, benzyl, dibenzyl, benzyloxycarbonyl, p-nitrobenzyloxycarbonyl, p-methoxybenzyloxycarbonyl, chloroacetyl, or trifluoroacetyl, the carboxy groups can be protected by radicals such as methoxymethyl, tert-butyl, benzhydryl, p-nitrobenzyl or p-methoxybenzyl, and the hydroxy groups can be protected by radicals such as benzyl, trityl, tetrahydropyranyl or 2-methoxy-prop-2-yl.

The various protective radicals can be removed simultaneously or successively.

By way of example,

1. The removal of the protective groups of amines is effected as follows:

in the case of a tert-butoxycarbonyl, trityl or p-methoxybenzyloxycarbonyl radical, by treatment in an acid medium. Preferably, trifluoroacetic acid is used and the process is carried out at a temperature of between 0° and 20° C., or anhydrous or aqueous formic acid, or para-toluenesulphonic or methanesulphonic acid, is used in acetone or acetonitrile at a temperature between 20° C. and the reflux temperature of the reaction mixture. Under these conditions, the compound of general formula I can be obtained in the form of the trifluoroacetate, the solvate with formic acid, the methanesulphonate or the para-toluenesulphonate, and from these the amine group can be liberated by any method which is in itself known for obtaining an amine from one of its salts without affecting the remainder of the molecule. In particular, the process is carried out by bringing the compound into contact with an ion exchange resin or by the action of an organic base.

In the case of a 2,2,2-trichloro-ethoxycarbonyl or p-nitrobenzyloxycarbonyl radical, by reduction (especially by treatment with zinc in acetic acid).

In the case of a chloroacetyl or trichloroacetyl radical, by applying the method described in the British Patent published under No. 1,454,589.

In the case of a benzyl, dibenzyl or benzyloxycarbonyl radical, by catalytic hydrogenation.

In the case of a trifluoroacetyl radical, by treatment in a basic medium.

2. The removal of the protective groups from the carboxy radical is effected as follows:

in the case of a tert-butyl, p-methoxybenzyl or benzhydryl radical, by treatment in an acid medium, under the conditions described above for the removal of the protective trityl radical from an amino group. In the case of the benzhydryl radical, the process can be carried out in the presence of anisole.

In the case of a methoxymethyl group, by treatment in a dilute acid medium.

In the case of a p-nitrobenzyl group, by reduction (especially by treatment with zinc in acetic acid, or by hydrogenolysis).

3. The removal of the protective groups from the hydroxy radicals is effected as follows:

in the case of a benzyl, trityl or tetrahydropyranyl group, by acidolysis, for example with trifluoroacetic acid, aqueous or non-aqueous formic acid or para-toluene-sulphonic acid.

In the case of the 2-methoxy-prop-2-yl-group, in accordance with the method described in British Pat. No. 2021561.

It will be understood that it may be desirable to change the nature of one or more of the substituents at an appropriate stage during the synthesis of the compounds of the invention, for example, the compounds of general formula I wherein $R^1$ or $R^3$ represents an amino group may be alternatively prepared from the corresponding compounds of general formula I wherein $R^1$ or $R^3$ represents a nitro group by the application or adaptation of known methods for such conversion. Compounds of general formula I wherein $R^1$ or $R^3$ represents an amino group may be transformed to diazonium salts, which are useful in synthesis as described in Morrison and Boyd's "Organic Chemistry" (1959), and thence to, for example, an iodine atom.

The following Examples and Reference Examples illustrate the preparation of the compounds of the present invention.

EXAMPLE 1

Compound A

2-Amino-N-(3-imidazol-1-ylpropyl)benzamide (32.9 g) was dissolved in pyradine (165 ml) and 4-chlorobenzenesulphonyl chloride (41.2 g) was added in portions. The temperature of the reaction mixture rose to 52° C. The solution was stirred at room temperature for 4 hours and poured into water (1.5 l) to precipitate an oil which slowly solidified on standing. The solid was collected, washed with water and recrystallised from ethanol to give 2-(4-chlorobenzenesulphonamido)-N-(3-imidazol-1-ylpropyl)-benzamide (24.4 g), in the form of a white solid, m.p. 175°–177° C.

(i) 2-Amino-N-(3-imidazol-1-ylpropyl)benzamide used as starting material above was prepared as follows:

Isatoic anhydride (22.0 g) was added in portions to a stirred solution of 3-imidazol-1-ylpropylamine (17.2 g) in dioxan (100 ml) over a period of 15 minutes. Stirring was continued for 40 minutes before the solution was evaporated in vacuo to give 2-amino-N-(3-imidazol-1-ylpropyl)benzamide as a buff coloured solid, used without further purification.

EXAMPLES 2–12

By proceeding in a similar manner to that described in Example 1 for the preparation of 2-(4-chlorobenzenesulphonamido)-N-(3-imidazol-1-ylpropyl)benzamide but replacing 4-chlorobenzenesulphonyl chloride or 2-amino-N-(3-imidazol-1-ylpropyl)benzamide by the indicated starting materials, the following compounds of general formula I were prepared (the compound letter is given in parenthesis):

2 (B): 2-(3-chlorobenzenesulphonamido)-N-(3-imidazol-1-ylpropyl)benzamide (white solid, m.p. 139°–142° C.): starting material, 3-chlorobenzenesulphonyl chloride 3 (C): 2-(2-chlorobenzenesulphonamido)-N-(3-imidazol-1-yl-propyl)benzamide (off-white solid, m.p. 154°–158° C.): starting material, 2-chlorobenzenesulphonyl chloride 4 (D): 2-(4-bromobenzenesulphonamido)-N-(3-imidazol-1-ylpropyl)benzamide (white solid, m.p. 178°–180° C.): starting material, 4-bromobenzenesulphonyl chloride 5 (E): 2-(benzenesulphonamido)-N-(3-imidazol-1-ylpropyl)benzamide (off-white solid, m.p. 112°–114° C.): starting material, benzenesulphonyl chloride 6 (F): 2-(4-methylbenzenesulphonamido)-N-(3-imidazol-1-yl-propyl)benzamide (off-white solid, m.p. 147°–149° C.): starting material, 4-methylbenzenesulphonyl chloride 7 (G): 2-(3,4-dimethylbenzenesulphonamido)-N-(3-imidazol-1-ylpropyl)benzamide (white solid, m.p. 172°–174° C.): starting material, 3,4-dimethylbenzenesulphonyl chloride 8 (H): 2-(4-nitrobenzenesulphonamido)-N-(3-imidazol-1yl-propyl)benzamide (fawn coloured solid, m.p. 148°–150° C.): starting material, 4-nitrobenzenesulphonyl chloride
9 (I): 5-chloro-2-(4-chlorobenzenesulphonamido)-N-(3-imidazol-1-ylpropyl)benzamide (white solid, m.p. 125°–128° C.): starting material, 5-chloro-2-amino-N-(3-imidazol-1-ylpropyl)benzamide
10 (J): 2-(2,5-dichlorobenzenesulphonamido)-N-(3-imidazol-1-ylpropyl)benzamide (pale brown solid, m.p. 198°–200° C.): starting material, 2,5-dichlorobenzenesulphonyl chloride
11 (K): 2-(2-nitrobenzenesulphonamido)-N-(3-imidazol-1-ylpropyl)benzamide (pale brown solid, m.p. 145°–147° C.): starting material, 2-nitrobenzenesulphonyl chloride
12 (L): 2-(4-fluorobenzenesulphonamido)-N-(3-imidazol-1-ylpropyl)benzamide (white solid, m.p. 117°–118° C.): starting material, 4-fluorobenzenesulphonyl chloride

EXAMPLE 13

Compound M

2-Amino-N-[3-(2-methylimidazol-1-yl)propyl]benzamide (10.5 g) was dissolved in pyridine (50 ml) and 4-chlorobenzenesulphonyl chloride (12.35 g) was added in portions during five minutes. The temperature of the reaction mixture rose to 45° C. The solution was stirred at room temperature for 4 hours and the pyridine was evaporated in vacuo to give a brown oil. The oil was chromatographed on silica gel, eluting with a mixture of chloroform and methanol (19:1) to give 2-(4-chlorobenzenesulphonamido)-N-[3-(2-methylimidazol-1-yl)propyl]benzamide in the form of a white solid (7 g), m.p. 122°–123° C.

2-Amino-N-[3-(2-methylimidazol-1-yl)propyl]benzamide used as starting material above was prepared by proceeding in a similar manner to that hereinbefore described in Example 1(i) for the preparation of 2-amino-N-(3-imidazol-1-ylpropyl)benzamide but replacing 3-imidazol-1-ylpropylamine by 3-(2-methylimidazol-1-yl)propylamine. 2-Amino-N-[3-(2-methylimidazol-1-yl)propyl]benzamide was recovered in the form of an oil which was used without further purification.

EXAMPLE 14

Compound N

By proceeding in a similar manner to that hereinbefore described in Example 1 for the preparation of 2-(4-chlorobenzenesulphonamido)-N-(3-imidazol-1-ylpropyl)benazmide but replacing 2-amino-N-(3-imidazol-1-ylpropyl)benzamide by 2-amino-N-[3-(4-methylimidazol-1-yl)propyl]benzamide there was prepared 2-(4-chlorobenzenesulphonamido)-N-[3-(4-methylimidazol-1-yl)propyl]benzamide in the form of a white solid, m.p. 123°–125° C.

2-Amino-N-[3-(4-methylimidazol-1-yl)propyl]benzamide used as starting material above was prepared by proceeding in a similar manner to that hereinbefore described in Example 1(i) for the preparation of 2-amino-N-(3-imidazol-1-ylpropyl)benzamide but replacing 3-imidazol-1-ylpropylamine by 3-(4-methylimidazol-1-yl)propylamine.

2-Amino-N-[3-(4-methylimidazol-1-yl)propyl]benzamide was recovered in the form of an oil which was used without further purification.

EXAMPLE 15

Compound O

By proceeding in a similar manner to that hereinbefore described in Example 14 for the preparation of 2-(4-chlorobenzenesulphonamido)-N-[3-(4-methylimidazol-1-yl)propyl]benzamide but replacing 4-chlorobenzenesulphonyl chloride by 4-nitrobenzenesulphonyl chloride, there was prepared 2-(4-nitrobenzenesulphonamido)-N-[3-(4-methylimidazol-1-yl) propyl]benzamide in the form of a yellow solid, m.p. 153°–155° C.

EXAMPLE 16

Compound P 2-(4-Nitrobenzenesulphonamido)-N-(3-imidazol-1-ylpropyl)benzamide (38.4 g) was dissolved in glacial acetic acid (30 ml) and 5% w/w palladium-on-charcoal (8.0 g) was added. The mixture was stirred under an atmosphere of hydrogen for 4 hours, filtered free of catalyst and evaporated. The solid residue was dissolved in water and the solution was adjusted to pH 9 by the addition of aqueous ammonia. The solid which had precipitated was collected and recrystallised from ethanol to give 2-(4-aminobenzenesulphonamido)-N-(3-imidazol-1-ylpropyl)benzamide (26.7 g) in the form of a white solid, m.p. 171°–175° C.

2-(4-Nitrobenzenesulphonamido)-N-(3-imidazol-1-ylpropyl)benzamide used above was prepared as hereinbefore described in Example 8.

EXAMPLE 17

Compound A

4-Chlorobenzenesulphonyl chloride (1.56 g) was added in portions over 2 minutes to a solution of 2-amino-N-(3-imidazol-1-ylpropyl)benzamide (1.8 g) in water (50 ml) at 80° C. on a steam bath. The mixture was stirred at 80°–90° C. for 3 hours, cooled to room temperature and brought to pH 7 with saturated aqueous sodium bicarbonate solution. The crude product which had precipitated was extracted into dichloromethane (2×100 ml); the resulting solution was dried over magnesium sulphate and evaporated to give a solid. The solid was recrystallised from ethanol to give 2-(4-chlorobenzenesulphonamido)-N-(3-imidazol-1-ylpropyl)benzamide (1.4 g), in the form of a white solid, m.p. 174°–176° C.

EXAMPLE 18

Compound A 2-(4-Chlorobenzenesulphonamido)benzoyl chloride (3.40 g) was added in portions to a stirred mixture of 3-imidazol-1-ylpropylamine (1.29 g), triethylamine (1.04 g) and dimethylformamide (25 ml) at room temperature. The temperature of the mixture rose to 33° C.; the mixture was then stirred at room temperature for 4 hours before pouring into water (500 ml). The aqueous solution was decanted from the crude product which had precipitated as a gum. This gummy material was dissolved in dichloromethane (50 ml), the solution was dried over magnesium sulphate and the solution was evaporated. The crude product was recrystallised from ethyl acetate to give 2-(4-chlorobenzenesulphonamido)-N-(3-imidazol-1-ylpropyl)benzamide, in the form of a white solid, m.p. 175°–177° C. (yield: 2.1 g).

EXAMPLES 19-50

By proceeding in a similar manner to that described in Example 1 for the preparation of 2-(4-chlorobenzenesulphonamido)-N-(3-imidazol-1-ylpropyl)benzamide but replacing 4-chlorobenzenesulphonyl chloride and/or 2-amino-N-(3-imidazol-1-ylpropyl)benzamide by the indicated starting material, the following compounds of general formula I were prepared (the compound letter is given in parenthesis):

19 (Q): 2-(4-methoxybenzenesulphonamido)-N-(3-imidazol-1-ylpropyl)benzamide (white solid, m.p. 179°-181° C.): starting material, 4-methoxybenzenesulphonyl chloride 20 (R): 2-(4-acetamidobenzenesulphonamido)-N-(3-imidazol-1-ylpropyl)benzamide (white solid, m.p. 192°-194° C.): starting material, 4-acetamidobenzenesulphonyl chloride 21 (S): 2-(4-isopropylbenzenesulphonamido)-N-(3-imidazol-1-ylpropyl)benzamide (white solid, m.p. 160°-162° C.): starting material, 4-isopropylbenzenesulphonyl chloride 22 (T): 2-(4-t-butylbenzenesulphonamido)-N-(3-imidazol-1-yl-propyl)benzamide (white solid, m.p. 163°-166° C.): starting material, 4-t-butylbenzenesulphonyl chloride 23 (U): 2-(4-octylbenzenesulphonamido)-N-(3-imidazol-1-yl-propyl)benzamide (white solid, m.p. 109°-111° C.): starting material, 4-octylbenzenesulphonyl chloride 24 (V): 2-(4-ethoxycarbonylbenzenesulphonamido)-N-(3-imidazol-1-ylpropyl)benzamide (off-white solid, m.p. 156°-158° C.): starting material, 4-ethoxycarbonylbenzenesulphonyl chloride 25 (W): 2-(3-trifluoromethylbenzenesulphonamido)-N-(3-imidazol-1-ylpropyl)benzamide (white solid, m.p. 133°-137° C.): starting material, 3-trifluoromethylbenzenesulphonyl chloride 26 (X): 2-(3,4-dichlorobenzenesulphonamido)-N-(3-imidazol-1-ylpropyl)benzamide (white solid, m.p. 164°-167° C.): starting material, 3,4-dichlorobenzenesulphonyl chloride 27 (Y): 2-(2,4-dichlorobenzenesulphonamido)-N-(3-imidazol-1-ylpropyl)benzamide (off-white solid, m.p. 152°-155° C.): starting material, 2,4-dichlorobenzenesulphonyl chloride 28 (Z): 2-(2,6-dichlorobenzenesulphonamido)-N-(3-imidazol-1-ylpropyl)benzamide (off-white solid, m.p. 203°-205° C.): starting material, 2,6-dichlorobenzenesulphonyl chloride 29 (AA): 2-(2,3-dichlorobenzenesulphonamido)-N-(3-imidazol-1-ylpropyl)benzamide (off-white solid, m.p. 153°-155° C.): starting material, 2,3-dichlorobenzenesulphonyl chloride 30 (BB): 2-(2-trifluoromethylbenzenesulphonamido)-N-(3-imidazol-1-ylpropyl)benzamide (fawn solid, m.p. 173°-175° C.): starting material, 2-trifluoromethylbenzenesulphonyl chloride 31 (CC): 2-(4-chloro-2-trifluoromethylbenzenesulphonamido)-N-(3-imidazol-1-ylpropyl)benzamide (off-white solid, m.p. 155°-157° C.): starting material, 4-chloro-2-trifluoromethylbenzenesulphonyl chloride 32 (DD): 2-(3,5-bistrifluoromethylbenzenesulphonamido)-N-(3-imidazol-1-ylpropyl)benzamide (off-white solid, m.p. 109° C.): starting material, 3,5-bistrifluoromethylbenzenesulphonyl chloride 33 (EE): 2-(2,4,5-trichlorobenzenesulphonamido)-N-(3-imidazol-1-ylpropyl)benzamide (off-white solid, m.p. 190°-200° C.): starting material, 2,4,5-trichlorobenzenesulphonyl chloride 34 (FF): 2-(2,3,4-trichlorobenzenesulphonamido)-N-(3-imidazol-1-ylpropyl)benzamide (off-white solid, m.p. 195°-197° C.): starting material, 2,3,4-trichlorobenzenesulphonyl chloride 35 (GG): 2-(4-chloro-3-trifluoromethylbenzenesulphonamido)-N-(3-imidazol-1-ylpropyl)benzamide (white solid, m.p. 148°-151° C.): starting material, 4-chloro-3-trifluoromethylbenzenesulphonyl chloride 36 (HH): 5-chloro-2-(3-trifluoromethylbenzenesulphonamido)-N-(3-imidazol-1-ylpropyl)benzamide (white solid, m.p. 159°-160° C.): starting materials, 5-chloro-2-amino-N-(3-imidazol-1-ylpropyl)benzamide and 3-trifluoromethylbenzenesulphonyl chloride 37 (II): 5-chloro-2-(3,5-bistrifluoromethylbenzenesulphonamido)-N-(3-imidazol-1-ylpropyl)benzamide (white solid, m.p. 149°-150° C.): starting materials, 5-chloro-2-amino-N-(3-imidazol-1-ylpropyl)benzamide and 3,5-bistrifluoromethylbenzenesulphonyl chloride 38 (JJ): 5-chloro-2-(3-chlorobenzenesulphonamido)-N-(3-imidazol-1-ylpropyl)benzamide (white solid, m.p. 124°-126° C.): starting materials, 5-chloro-2-amino-N-(3-imidazol-1-ylpropyl)benzamide and 3-chlorobenzenesulphonyl chloride 39 (KK): 2-(3-fluorobenzenesulphonamido)-N-(3-imidazol-1-ylpropyl)benzamide (white solid, m.p. 147°-149° C.): starting material, 3-fluorobenzenesulphonyl chloride 40 (LL): 2-(3-fluoro-4-methylbenzenesulphonamido)-N-(3-imidazol-1-ylpropyl)benzamide (off-white solid, m.p. 155°-157° C.): starting material, 3-fluoro-4-methylbenzenesulphonyl chloride 41 (MM): 2-(3-bromobenzenesulphonamido)-N-(3-imidazol-1-ylpropyl)benzamide (white solid, m.p. 146°-148° C.): starting material, 3-bromobenzenesulphonyl chloride 42 (NN): 2-(3-nitrobenzenesulphonamido)-N-(3-imidazol-1-ylpropyl)benzamide (fawn solid, m.p. 160°-162° C.): starting material, 3-nitrobenzenesulphonyl chloride 43 (OO): 2-(2,4-difluorobenzenesulphonamido)-N-(3-imidazol-1-ylpropyl)benzamide (cream-coloured solid, m.p. 122°-124° C.): starting material, 2,4-difluorobenzenesulphonyl chloride 44 (PP): 2-(3-methylbenzenesulphonamido)-N-(3-imidazol-1-ylpropyl)benzamide (off-white solid, m.p. 160°-161° C.): starting material, 3-methylbenzenesulphonyl chloride 45 (QQ): 2-(2-methylbenzenesulphonamido)-N-(3-imidazol-1-ylpropyl)benzamide (white solid, m.p. 139°-141° C.): starting material, 2-methylbenzenesulphonyl chloride 46 (RR): 2-(2-fluorobenzenesulphonamido)-N-(3-imidazol-1-ylpropyl)benzamide (off-white solid, m.p. 115°-117° C.): starting material, 2-fluorobenzenesulphonyl chloride 47 (SS): 2-(2-chloro-5-trifluoromethylbenzenesulphonamido)-N-(3-imidazol-1-ylpropyl)benzamide (pale-brown solid, m.p. 181°-184° C.): starting material, 2-chloro-5-trifluoromethylbenzenesulphonyl chloride 48 (UU): 2-(4-chlorobenzenesulphonamido)-N-(4-imidazol-1-ylbutyl)benzamide (off-white solid, m.p. 131°–133° C.): starting material, 2-amino-N-(4-imidazol-1-ylbutyl)benzamide 49 (VV): 2-(4-chlorobenzenesulphonamido)-N-(2-imidazol-1-ylethyl)benzamide (white solid, m.p. 130°–133° C.): starting material, 2-amino-N-(2-imidazol-1-ylethyl)benzamide 50 (WW): (±)-2-(4-chlorobenzenesulphonamido)-N-(3-imidazol-1-ylbutyl)benzamide (white solid, m.p. 150°–153° C.): starting material, (±)-2-amino-N-(3-imidazol-1-ylbutyl)benzamide

EXAMPLE 51

Compound TT

A solution of 2-(4-aminobenzenesulphonamido)-N-(3-imidazol-1-ylpropyl)benzamide (11.0 g; hereinbefore prepared in Example 16) in a mixture of concentrated hydrochloric acid (9.5 ml) and water (50 ml) was cooled to between 0° C. and 5° C. whilst a solution of sodium nitrite (2.09 g) in water (15 ml) was added dropwise over 15 minutes. A solution of potassium iodide (4.58 g) in water (10 ml) was then added over 30 minutes, maintaining a temperature between 0° C. and 10° C. The mixture was then heated at 95° C. for 15 minutes. The resultant solution was cooled and adjusted to pH 8 by dropwise addition of 10% w/v aqueous sodium hydroxide solution. The solid precipitate was collected, washed with water and recrystallised from ethyl acetate to give 2-(4-iodobenzenesulphonamido)-N-(3-imidazol-1-ylpropyl)benzamide in the form of a pale-yellow solid, m.p. 162°–166° C. (yield: 3.4 g).

EXAMPLE 52

Compound W hydrochloride 2-(3-Trifluoromethylbenzenesulphonamido)-N-(3-imidazol-1-ylpropyl)benzamide (9.0 g) was dissolved in hot isopropanol (90 ml). Concentrated aqueous hydrochloric acid (2.0 ml) was added. The resultant solution was evaporated to yield an oil which was recrystallised from ethyl acetate to give 2-(3-trifluoromethylbenzenesulphonamido)-N-(3-imidazol-1-ylpropyl)benzamide hydrochloride (9.3 g) in the form of a white solid, m.p. 173°–175° C.

REFERENCE EXAMPLE 1

2-Methylamino-N-(3-imidazol-1-ylpropyl)benzamide which may be used as starting material was prepared as follows:

N-Methylisatoic anhydride (17.7 g) was added in portions to a stirred solution of 3-imidazol-1-ylpropylamine (12.5 g) in dioxan (150 ml) over a period of 15 minutes. Stirring was continued for 40 minutes before the solution was evaporated in vacuo to give 2-methylamino-N-(3-imidazol-1-ylpropyl)benzamide (18.0 g), in the form of a buff coloured solid, m.p. 138°–141° C., after recrystallisation from isopropanol.

2-Methylamino-N-(3-imidazol-1-ylpropyl)benzamide may be used to replace the 2-amino-N-(3-imidazol-1-ylpropyl) benzamides used as starting material in the foregoing Examples to prepare corresponding compounds of general formula I in which $R^2$ represents a methyl group.

REFERENCE EXAMPLE 2

5-Chloro-2-amino-N-(3-imidazol-1-ylpropyl)benzamide used as starting material in Example 9 was prepared as follows:

5-Chloroisatoic anhydride (26.7 g) was added in portions to a stirred solution of 3-imidazol-1-ylpropylamine (17.2 g) in dioxan (150 ml) over a period of 15 minutes. Stirring was continued for 40 minutes before the solution was evaporated in vacuo to give 5-chloro-2-amino-N-(3-imidazol-1-ylpropyl)benzamide as a buff coloured solid, used without further purification.

2-Amino-N-(4-imidazol-1-ylbutyl)benzamide used as starting material in Example 48 was prepared by proceeding in a similar manner to that hereinbefore described in Example 1 (i) for the preparation of 2-amino-N-(3-imidazol-1-ylpropyl)benzamide but replacing 3-imidazol-1-ylpropylamine by 4-imidazol-1-ylbutylamine.

2-Amino-N-(4-imidazol-1-ylbutyl)benzamide was recovered in the form of an oil which was used without further purification.

2-Amino-N-(2-imidazol-1-ylethyl)benzamide used as starting material in Example 49 was prepared by proceeding in a similar manner to that hereinbefore described in Example 1(i) for the preparation of 2-amino-N-(3-imidazol-1-ylpropyl)benzamide but replacing 3-imidazol-1-ylpropylamine by 2-imidazol-1-ylethylamine.

2-Amino-N-(2-imidazol-1-ylethyl)benzamide was recovered in the form of an oil which was used without further purification.

(±)-2-Amino-N-(3-imidazol-1-ylbutyl)benzamide used as starting material in Example 50 was prepared by proceeding in a similar manner to that hereinbefore described in Example 1(i) for the preparation of 2-amino-N-(3-imidazol-1-ylpropyl)benzamide but replacing 3-imidazol-1-ylpropylamine by (±)-3-imidazol-1-ylbutylamine.

(±)-2-Amino-N-(3-imidazol-1-ylbutyl)benzamide was recovered in the form of an oil which was used without further purification.

The present invention includes within its scope pharmaceutical compositions which comprise at least one of the compounds of general formula I or a pharmaceutically acceptable salt thereof in association with a pharmaceutically acceptable carrier or coating. In clinical practice the compounds of the present invention may be administered parenterally, but are preferably administered rectally or, more preferably, orally.

Solid compositions for oral administration include compressed tablets, pills, powders and granules. In such solid compositions, one or more of the active compounds is, or are, admixed with at least one inert diluent such as starch, sucrose or lactose. The compositions may also comprise, as is normal practice, additional substances other than inert diluents, e.g. lubricating agents, such as magnesium stearate.

Liquid compositions for oral administration include pharmaceutically acceptable emulsions, solutions, suspensions, syrups and elixirs containing inert diluents commonly used in the art such as water and liquid paraffin. Besides inert diluents such compositions may comprise adjuvants, such as wetting, and suspending agents, and sweetening, flavouring, perfuming and preserving agents. The compositions according to the invention for oral administration also include capsules of absorbable material such as gelatin, containing one or more of the active substances with or without the addition of diluents or excipients.

Preparations according to the invention for parenteral administration include sterile aqueous, aqueous-organic, and organic solutions, suspensions and emulsions. Examples of organic solvents or suspending media are propylene glycol, polyethylene glycol, vegetable oils such as olive oil and injectable organic esters such as ethyl oleate. The compositions may also contain adjuvants such as stablising, preserving, wetting, emulsifying and dispersing agents. They may be sterilized by, for example, filtration through a bacteria-retaining filter, by incorporation in the compositions of sterilizing agents, by irradiation or by heating. They may also be manufactured in the form of sterile solid compositions, which can be dissolved in sterile water or some other sterile injectable medium immediately before use.

Solid compositions for rectal administration include suppositories formulated in accordance with known methods and containing one or more of the compounds of formula I or a pharmaceutically acceptable salt thereof.

The percentage of active ingredient in the compositions of the invention may be varied, it being necessary that it should constitute a proportion such that a suitable dosage shall be obtained. Obviously, several unit dosage forms may be administered at about the same time. The dose employed will be determined by the physician, and depends upon the desired therapeutic effect, the route of administration and the duration of the treatment, and the condition of the patient. In the adult, the doses are generally between 0.1 and 50 mg/kg body weight per day by oral administration. For example, in the treatment of diabetes between 5 and 40 mg/kg body weight per day by oral administration, and as hypolipidaemic agents between 10 and 50 mg/kg body weight per day by oral administration.

The following Example illustrates pharmaceutical compositions according to the present invention.

EXAMPLE 53

No. 2 size gelatin capsules each containing:

| | |
|---|---|
| 2-(4-chlorobenzenesulphonamido)-N—(3-imidazol-1-ylpropyl)benzamide | 20 mg |
| lactose | 100 mg |
| starch | 60 mg |
| dextrin | 40 mg |
| magnesium stearate | 1 mg | were prepared in accordance with the usual procedure.
We claim:

1. A benzamide derivative of the formula:

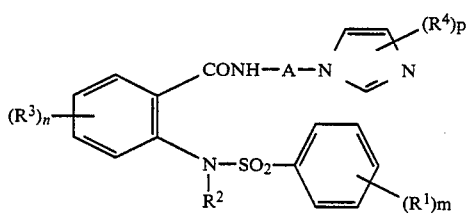

wherein A represents a divalent straight- or branched-chain alkylene group containing from 1 to 6 carbon atoms and $R^1$ represents a halogen atom or a hydroxy, mercapto, amino, nitro, cyano, carboxy or carbamoyl group or an alkyl, fluorine-substituted alkyl, alkoxy, alkylthio, alkylsulphinyl, alkylsulphonyl, alkoxycarbonyl, alkylamino, dialkylamino, alkylcarbamoyl, dialkylcarbamoyl, alkanoyl, alkanoyloxy or alkanoylamino group and m represents zero or the integer 1, 2 or 3, $R^2$ represents a hydrogen atom or an alkyl group, $R^3$ represents a halogen atom or a hydroxy, amino, nitro, cyano, carboxy or carbamoyl group or an alkyl, fluorine-substituted alkyl, alkoxy, alkoxycarbonyl, dialkylamino, alkylcarbamoyl or alkanoylamino group and n represents zero or the integer 1 or 2, $R^4$ represents an alkyl radical and p represents zero or the integer 1 or 2, alkyl groups, alkoxy groups and alkanoyl groups within the definitions of $R^1$, $R^2$, $R^3$ and $R^4$ being straight- or branched-chain and containing from 1 to 10 carbon atoms, or a pharmaceutically acceptable salt thereof.

2. A benzamide derivative according to claim 1, wherein A represents a divalent straight- or branched-chain alkyl group containing 2, 3 or 4 carbon atoms, or a pharmaceutically acceptable salt thereof.

3. A benzamide derivative according to claim 1, wherein alkyl groups, alkoxy groups and alkanoyl groups contain from 1 to 4 carbon atoms, or a pharmaceutically acceptable salt thereof.

4. A benzamide derivative according to claim 1, wherein A represents an ethylene, trimethylene, 3-methyltrimethylene or tetramethylene group and $R^1$ represents a halogen atom or an amino, nitro, trifluoromethyl or acetamido group or an alkyl, alkoxycarbonyl or $C_{1-4}$ alkoxy group and m represents zero or the integer 1, 2 or 3, $R^2$ represents a hydrogen atom, $R^3$ represents a halogen atom and n represents zero or the integer 1, and $R^4$ represents an alkyl group in the 2- or 4-position and p represents zero or the integer 1, or a pharmaceutically acceptable salt thereof.

5. A benzamide derivative according to claim 1, wherein A represents an ethylene, trimethylene or 3-methyltrimethylene group and $R^1$ represents a halogen atom, trifluoromethyl group, or an alkyl group and m represents the integer 1 or 2, $R^2$ represents a hydrogen atom, $R^3$ represents a halogen atom and n represents zero or the integer 1, and $R^4$ represents an alkyl group in the 4-position and p represents zero or the integer 1, or a pharmaceutically acceptable salt thereof.

6. A benzamide derivative according to claim 5, wherein m is the integer 1 and the group $R^1$ is in the 2, 3 or 4-position, or the 3-position when $R^1$ represents a trifluoromethyl group, or a pharmaceutically acceptable salt thereof.

7. A benzamide derivative according to claim 5, wherein m is the integer 2 and the groups $R^1$ are the same and are in positions 2,4; 3,4 or 2,5 when $R^1$ represents halogen and in positions 3,4 when $R^1$ represents methyl, or a pharmaceutically acceptable salt thereof.

8. A benzamide derivative according to claim 1, wherein A represents a trimethylene group, or a pharmaceutically acceptable salt thereof.

9. A benzamide derivative according to claim 1, which is 2-(4-chlorobenzenesulphonamido)-N-(3-imidazol-1-ylpropyl)benzamide or a pharmaceutically acceptable salt thereof.

10. A benzamide derivative according to claim 1, which is 2-(3-trifluoromethylbenzenesulphonamido)-N-(3-imidazol-1-ylpropyl)benzamide or a pharmaceutically acceptable salt thereof.

11. The hydrochloride of the benzamide derivative claimed in claim 10.

12. A benzamide derivative of the formula:

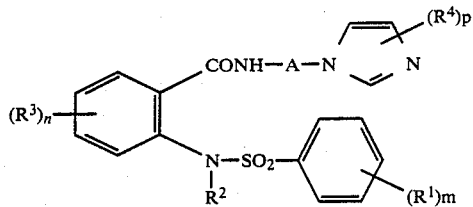

wherein A represents an ethylene, trimethylene, 3-methyltrimethylene or tetramethylene group and $R^1$ represents a halogen atom or an amino, nitro, trifluoromethyl or acetamido group or a methyl, $C_{2-11}$-alkoxycarbonyl or $C_{1-4}$ alkoxy group and m represents zero or the integer 1, 2 or 3, $R^2$ represents a hydrogen atom, $R^3$ represents a chlorine atom and n represents zero or the integer 1, and $R^4$ represents a methyl group in the 2- or 4-position and p represents zero or the integer 1, or a pharmaceutically acceptable salt thereof.

13. A hypoglycaemic composition useful in the prevention or treatment of diabetes, which comprises a hypoglycaemically effective amount of a benzamide derivative as claimed in claim 1 or a pharmaceutically acceptable salt thereof in association with a pharmaceutically acceptable carrier or coating.

14. A hypolipidaemic composition useful in the prevention or treatment of hyperlipoproteinaemic states, which comprises a hypolipidaemically effective amount of a benzamide dervative as claimed in claim 1 or a pharmaceutically acceptable salt thereof in association with a pharmaceutically acceptable carrier or coating.

* * * * *